United States Patent
Razi (10) Patent No.: US 10,774,357 B2
(45) Date of Patent: Sep. 15, 2020

(54) METHODS AND SYSTEMS FOR PREDICTING DRUG-RESPONSE

(71) Applicant: Nahid Razi, La Jolla, CA (US)

(72) Inventor: Nahid Razi, La Jolla, CA (US)

( * ) Notice: Subject to any disclaimer, the term of this patent is extended or adjusted under 35 U.S.C. 154(b) by 267 days.

(21) Appl. No.: 15/385,629

(22) Filed: Dec. 20, 2016

(65) Prior Publication Data

US 2017/0166949 A1 Jun. 15, 2017

Related U.S. Application Data (62) Division of application No. 14/380,064, filed as application No. PCT/US2013/027197 on Feb. 21, 2013, now abandoned.

(60) Provisional application No. 61/601,831, filed on Feb. 22, 2012.

(51) Int. Cl.
*G01N 33/574* (2006.01)
*C12Q 1/02* (2006.01)

(52) U.S. Cl.
CPC ....... *C12Q 1/025* (2013.01); *G01N 33/57492* (2013.01); *G01N 2333/42* (2013.01); *G01N 2333/46* (2013.01); *G01N 2333/705* (2013.01); *G01N 2400/40* (2013.01); *G01N 2800/44* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 5,171,667 A * | 12/1992 | Hakomori | C07K 16/30 424/137.1 |
| 5,227,160 A * | 7/1993 | Nudelman | A61K 35/52 424/137.1 |
| 2006/0223128 A1 | 10/2006 | Razi | |
| 2007/0265170 A1 | 11/2007 | Blixt | |
| 2012/0245235 A1 | 9/2012 | Rhodes | |

OTHER PUBLICATIONS

Dilruba et al, Cancer Chemother Pharmacol, 77:1103-1124, 2016.*
Kelland, Nat Rev Cancer, 7:573-584, 2007.*
Iwamori et al, J Biochem, 141:309-317, 2007.*
Zhou et al, Current Prot Pep Sci, 4:1-9, 2003.*
Nudelnnan et al, JBC 264:18719-18725, 1989.*
Baran et al., "Expression of multi drug resistance (MDR1) gene in human promyelocytic leukemia cell line selected with vincristine", Turkish Journal of Cancer, 2005, vol. 35, No. 2, pp. 88-92.
Ito et al. "Localization of binding sites of Ulex europaeus I, Helix pomatia and Griffonia simplicifolia 1-B4 lectins and analysis of their backbone structures by several glycosidases and poly-N-acetyllactosamine-specific lectins in human breast carcinomas". Histochem Cell Biol., 1996, 106(3): pp. 331-339, (abstract).
Ito et al., "Histochemical demonstration and analysis of poly-N-acetyllactosamine structure in normal and malignant human tissues", Histol Histopathol (1996) 11:203-214.
Nakahara et al., "Involvement of oligosaccharide changes in $\alpha 5\beta 1$ integrin in a cisplatin-resistant human squamous cell carcinoma cell line", Molecular Cancer Therapeutics, 2003, vol. 2, pp. 1207-1214.
Saitoh et al., "Differential glycosylation and cell surface expression of lysosomal membrane glycoproteins in sublines of a human colon cancer exhibiting distinct metastatic potentials", The Journal of Biological Chemistry, 1992, vol. 267, No. 8, pp. 5700-5711.

* cited by examiner

*Primary Examiner* — Mark Halvorson
(74) *Attorney, Agent, or Firm* — Knobbe, Martens, Olson & Bear, LLP (57) ABSTRACT

Disclosed herein are methods and systems for determining whether a cell is resistant to one or more drugs. Also, disclosed herein are methods and systems for monitoring the treatment of a cancer patient to determine whether the cancerous cells being treated are resistant to the treatment. Further, disclosed herein are methods and systems for predicting the responsiveness of a cell to a drug. Also, disclosed herein are methods and systems to determine the rate of the efficacy of a chemotherapeutic drug on a cancerous, neoplastic or damaged cells.

8 Claims, 3 Drawing Sheets

METHODS AND SYSTEMS FOR PREDICTING DRUG-RESPONSE

RELATED APPLICATIONS

This application is a divisional of U.S. patent application Ser. No. 14/380,064, filed Aug. 20, 2014, which is a U.S. National Phase under 35 U.S.C. § 371 of International Application No. PCT/US2013/027197, filed Feb. 21, 2013, which claims priority to U.S. Provisional patent application Ser. No. 61/601,831, entitled METHODS AND SYSTEMS FOR PREDICTING DRUG-RESPONSE, filed Feb. 22, 2012, the disclosure of each of which is incorporated herein by reference in its entirety.

TECHNICAL FIELD

In general, the present invention relates to the field of medicine and diagnosis. More particularly, this invention is relates to methods and systems of diagnosis, and companion diagnostics to predict drug efficacy.

BACKGROUND

Glycosylation is a post translational modification that is crucial in various stages of development, differentiation and oncogenesis (1-7). Glycan modification is a dynamic process involved in cell-signaling and cell-interaction. Glycans are receptors for a variety of ligands such as toxins, antibodies, bacteria, viruses, cellular receptors and lectins (8-18).

The first glycan biomarker for drug response and multidrug resistance was disclosed in U.S. Pat. No. 7,585,503, issued Sep. 8, 2009, which is incorporated herein by reference in its entirety (19). In brief, U.S. Pat. No. 7,585,503 describes flow cytometry to evaluate the distribution of cell surface sialic acids on isogenic cell line pairs, each pair comprising a drug-sensitive parental isotype and its drug-resistant off-spring phenotype. Comparison of the sialic acid profiles of each set of drug-susceptible and drug-resistant isogenic pairs revealed a distinct decrease in the amounts of alpha 2-6 sialic acid motif (hereinafter "AD6") on the surface of drug-resistant cells compared to their drug-sensitive isotypes in all of the isogenic cell pairs.

SUMMARY

Some embodiments of the systems and methods described herein include methods of determining whether cells from a patient are likely to be multiple drug resistant (MDR) neoplastic or damaged cells. In some embodiments the method comprises the steps of determining the amount of polyLacNAc (PLX or poly-N-acetyllactosamine) expressed on the surface of candidate MDR neoplastic or candidate damaged cells; the data from the PLX expression level of the candidate MDR neoplastic or the candidate damaged cells indicates the degree of drug responsiveness relative to the defined standard values for drug response by the same cell type as the candidate MDR neoplastic or the candidate damaged cells. In some such embodiments, the standard values for drug response can be defined by algorithms that are developed for drug response assessment, by analyzing the PLX expression levels of a statistically significant number of retrospective set of selected specimens from the same cell type of the candidate MDR neoplastic or the candidate damaged cells.

In some embodiments of the systems and methods described herein, algorithms for drug response assessments are developed from the PLX expression level analysis of a retrospective set of neoplastic or damaged cells, of the same cell types as the candidate neoplastic and damaged cells, obtained from the tissue repository systems with known characteristics of each specimens before starting treatment with chemotherapeutic drugs, as well as a known drug-response and characteristics of that neoplastic specimen after treatment with chemotherapeutic drugs after a defined period of follow up time.

In other embodiments of the systems and methods described herein, algorithms for drug response assessments are developed from the PLX expression level analysis of a set of neoplastic or damaged cells, of the same cell types as the candidate neoplastic or the candidate damaged cells, acquired from patients in a prospective manner, wherein the neoplastic cell specimens or damaged cell specimens are obtained from patients before starting treatment with chemotherapeutic drugs, and are monitored for a defined period of follow up time for the drug responsiveness after treatment with chemotherapeutic drugs.

In further embodiments of the systems and methods described herein, standard values for drug response are defined by analyzing the PLX expression level of a statistically significant number of retrospective set of selected specimens with a known history of drug response from the same cell type as the candidate MDR neoplastic or candidate damaged cells, comprising non-damaged and non-neoplastic cells, as well as the neoplastic specimens or damaged cell specimens from patients with known history of drug response. The information obtained from the analysis can be used to generate threshold levels for drug responsiveness based on the PLX expression levels.

In some embodiments, the defined standard values for drug responsiveness based on the PLX expression levels are adapted to a chart or diagram for drug response, wherein the degree of drug responsiveness of the candidate MDR neoplastic or the candidate damaged cells are determined relative to the drug response chart or diagram developed for a same cell type as the candidate MDR neoplastic or candidate damaged cells.

In some embodiments of the systems and methods described herein, determining the amount of PLX expressed on the surface of the candidate MDR neoplastic cells or on the surface of the candidate damaged cells comprises contacting the candidate MDR neoplastic cells or the candidate damaged cells with a PLX-binding agent. Certain embodiments of the methods described herein also include a step of measuring the amount of PLX-binding agent bound to PLX. In some embodiments, the PLX-binding agent comprises an agent selected from the group consisting of lectins, antibodies and other carbohydrate-specific binding compounds. In a preferred embodiment, the PLX-binding agent comprises a lectin from *Lycopersicon esculentum* (LEL).

In other embodiments of the systems and methods described herein, the PLX-binding agent comprises a label. In some embodiments, the label is selected from the group consisting of a fluorescent label, a chemiluminescent label, a radioactive label, a magnetic label, a paramagnetic label, a promagnetic label, a colorometric label, an electronic label and a digital label. In certain embodiments, the PLX is expressed on a glycoconjugate.

In some embodiments of the systems and methods described herein, the candidate MDR neoplastic cells are selected from the group consisting of carcinoma, lymphoma, melanoma, sarcoma, leukemia, retinoblastoma, myeloma, glioma, mesothelioma osteosarcoma, transitional cell carcinoma, squamous cell carcinoma (SCC), carcinomatosis and germinal specimens.

Additional embodiments of the systems and methods described herein relate to systems and methods for determining whether neoplastic cells from a cancerous tissue of a patient are likely to develop multiple drug resistance (MDR). In some such embodiments, the methods can comprise determining the amount of PLX expressed on the surface of a first sample of neoplastic cells from a cancerous tissue from a patient; the data from the first PLX expression level determination of the candidate neoplastic cells indicates the degree of drug responsiveness at a known stage of the disease relative to the defined standard values for drug response of the same cell type as the candidate neoplastic cells; then determining the amount of PLX expressed on the surface of a second sample of neoplastic cells from the cancerous tissue after a defined period of follow up time of treatment with a chemotherapeutic agent for cancer treatment; the data from the second PLX expression level of the candidate neoplastic cells indicates the degree of responsiveness at the a defined period of time after treatment with chemotherapeutic drugs. Comparison of the degree of responsiveness of the first PLX expression level and the second PLX expression level determines whether the neoplastic cells from a cancerous tissue of the patient are likely to develop multiple drug resistance (MDR.)

In some embodiments of the systems and methods described herein, the standard values for drug response are defined by algorithms that are developed for drug response assessment, by analyzing the PLX expression levels of a statistically significant number of retrospective set of selected specimens from the same cell type as the candidate neoplastic cells that are tested for developing multiple drug resistance.

In some embodiments, algorithms for drug response assessments are developed from the PLX expression level analysis of a retrospective set of neoplastic cells of the same cell types as the neoplastic cells that are candidates for developing MDR. The retrospective sets of neoplastic cells can be obtained from tissue repository systems with known characteristics of each specimen before starting treatment with chemotherapeutic drugs, as well as a known drug-response and characteristics of the neoplastic specimen after treatment with chemotherapeutic drugs after a defined period of follow up time.

In some embodiments, algorithms for drug response assessments are developed from the PLX expression level analysis of a set of neoplastic cells of the same cell types as the neoplastic cells that are candidates for developing MDR. The set of neoplastic cells can be acquired from patients in a prospective manner, wherein the neoplastic specimens are obtained from patients before starting treatment with chemotherapeutic drugs, and monitored for a defined period of follow up time for drug responsiveness after treatment with chemotherapeutic drugs.

In some embodiments of this systems and methods described herein, standard values for drug response are defined by analyzing the PLX expression level of a statistically significant number of retrospective set of selected specimens with a known history of drug response from the same cell type of the candidate MDR neoplastic cells, comprising non-damaged and non-neoplastic cells, as well as the neoplastic specimens from patients with known history of drug response. The information obtained from the analysis can be used to generate threshold levels for drug responsiveness based on the PLX expression levels.

In other embodiments, the defined standard values for drug responsiveness based on the PLX expression levels are adapted to a chart or diagram for drug response, wherein the degree of drug responsiveness of the neoplastic candidate for MDR development is determined relative to the drug response chart or diagram developed for a same cell type as the candidate MDR neoplastic or damaged cell.

Some embodiments of the systems and methods described herein relate to systems and methods for determining whether neoplastic cells from a cancerous tissue of a patient are likely to develop multiple drug resistance (MDR). In some such embodiments, the methods can comprise determining the amount of PLX expressed on the surface of a first sample of neoplastic cells from a cancerous tissue from a patient In some embodiments, determining the amount of PLX expressed on the surface of the neoplastic cells comprises contacting the neoplastic cells with a PLX-binding agent. Certain embodiments of the methods described herein also include a step of measuring the amount of PLX-binding agent bound to PLX. In some embodiments, the PLX-binding agent comprises an agent selected from the group consisting of lectins, antibodies and other carbohydrate-specific binding compounds. In a preferred embodiment, wherein the PLX-binding agent comprises a lectin from *Lycopersicon esculentum* (LEL).

In other embodiments of the methods described herein, the PLX-binding agent comprises a label. In some embodiments, wherein the label is selected from the group consisting of a fluorescent label, a chemiluminescent label, a radioactive label, a magnetic label, a paramagnetic label, a promagnetic label, a colorometric label, an electronic label and a digital label. In certain embodiments, wherein the PLX is expressed on a glycoconjugate.

In some embodiments of the methods described herein, the candidate MDR neoplastic cells or the candidate damaged cells are selected from the group consisting of carcinoma, lymphoma, melanoma, sarcoma, leukemia, retinoblastoma, myeloma, glioma, mesothelioma osteosarcoma, transitional cell carcinoma, squamous cell carcinoma (SCC), carcinomatosis and germinal specimens.

Further embodiments of the present invention include methods of determining whether neoplastic cells are likely to be multiple drug resistant (MDR) neoplastic cells. In some embodiments the methods can comprise determining the amount of PLX expression on the surface of candidate MDR neoplastic cells; the data from the PLX expression level of the candidate MDR neoplastic cells indicates the degree of drug responsiveness relative to the defined standard values for drug response by the same cell type as the candidate MDR neoplastic cells. The standard values for drug response can be defined by algorithms that are developed for drug response assessment, by analyzing the PLX expression levels of a statistically significant number of retrospective set of selected specimens from the same cell type of the candidate MDR neoplastic or damaged cells.

In some embodiments, algorithms for drug response assessments are developed from the PLX expression level analysis of a retrospective set of neoplastic cells, of the same cell types as the candidate neoplastic cells, that are obtained from the tissue repository systems with known characteristics of each specimens before starting treatment with chemotherapeutic drugs, as well as a known drug-response and characteristics of the neoplastic specimen after treatment with chemotherapeutic drugs after a defined period of follow up time.

In another embodiments, algorithms for drug response assessments are developed from the PLX expression level analysis of a set of neoplastic cells, of the same cell types as the candidate neoplastic cells, are acquired from patients in a prospective manner, wherein the neoplastic specimens are obtained from patients before starting treatment with chemotherapeutic drugs, and monitored for a defined period of follow up time for the drug responsiveness after treatment with chemotherapeutic drugs.

In some embodiments of this invention, standard values for drug response are defined by analyzing the PLX expression level of a statistically significant number of retrospective set of selected specimens with a known history of drug response from the same cell type of the candidate MDR neoplastic cells, comprising non-damaged and non-neoplastic cells, as well as the neoplastic specimens from patients with known history of drug response. The information obtained from the analysis can be used to generate threshold levels for drug responsiveness based on the PLX expression levels.

In some embodiments, the defined standard values for drug responsiveness based on the PLX expression levels are adapted to a chart or diagram for drug response, wherein the degree of drug responsiveness of the candidate MDR neoplastic cell are determined relative to the drug response chart or diagram developed for a same cell type as the candidate MDR neoplastic cell.

In some embodiments, determining the amount of PLX expressed on the surface of the candidate MDR neoplastic cells comprises contacting the candidate MDR neoplastic cells with a PLX-binding agent. Certain embodiments of the methods described herein also include a step of measuring the amount of PLX-binding agent bound to PLX. In some embodiments, the PLX-binding agent comprises an agent selected from the group consisting of lectins, antibodies and other carbohydrate-specific binding compounds. In a preferred embodiment, the PLX-binding agent comprises a lectin from *Lycopersicon esculentum* (LEL).

In other embodiments of the methods described herein, the PLX-binding agent comprises a label. In some embodiments, the label is selected from the group consisting of a fluorescent label, a chemiluminescent label, a radioactive label, a magnetic label, a paramagnetic label, a promagnetic label, a colorometric label, an electronic label and a digital label. In certain embodiments, the PLX is expressed on a glycoconjugate.

In some embodiments of the methods described herein, the candidate MDR neoplastic cells are selected from the group consisting of carcinoma, lymphoma, melanoma, sarcoma, leukemia, retinoblastoma, myeloma, glioma, mesothelioma osteosarcoma, transitional cell carcinoma, squamous cell carcinoma (SCC), carcinomatosis and germinal specimens.

Further embodiments of the present invention relate to methods of predicting the effectiveness of a drug on neoplastic cells from a patient. In some embodiments, the methods comprise the steps of determining the amount of PLX expression on the surface of the neoplastic cells from the patient; the data from the PLX expression level of the candidate neoplastic cells indicates the degree of drug responsiveness relative to the defined standard values for drug response by the same cell type as the candidate neoplastic cells from patient. The standard values for drug response are defined by algorithms that are developed for drug response assessment, by analyzing the PLX expression levels of a statistically significant number of retrospective set of selected specimens from the same cell type of the candidate neoplastic cells.

In some embodiments, algorithms for drug response assessments are developed from the PLX expression level analysis of a retrospective set of neoplastic cells, of the same cell types as the candidate neoplastic cells, that are obtained from the tissue repository systems with known characteristics of each specimen before starting treatment with chemotherapeutic drugs, as well as a known drug-response and characteristics of the neoplastic specimen after treatment with chemotherapeutic drugs of a defined period of follow up time.

In another embodiments, algorithms for drug response assessments are developed from the PLX expression level analysis of a set of neoplastic cells, of the same cell types as the candidate neoplastic cells, are acquired from patients in a prospective manner, wherein the neoplastic specimens are obtained from patients before starting treatment with chemotherapeutic drugs, and monitored for a defined period of follow up time for the drug responsiveness after treatment with chemotherapeutic drugs.

In some embodiments of this invention, standard values for drug response are defined by analyzing the PLX expression level of a statistically significant number of retrospective set of selected specimens with a known history of drug response from the same cell type of the candidate neoplastic cells, comprising non-damaged and non-neoplastic cells, as well as the neoplastic specimens from patients with known history of drug response. The information obtained from the analysis can be used to generate threshold levels for drug responsiveness based on the PLX expression levels.

In some embodiments, the defined standard values for drug responsiveness based on the PLX expression levels are adapted to a chart or diagram for drug response, wherein the degree of drug responsiveness of the candidate neoplastic cell are determined relative to the drug response chart or diagram developed for a same cell type as the candidate neoplastic cell.

In some embodiments of the methods described herein, determining the amount of PLX expressed on the surface of the neoplastic cells from the patient comprises contacting the neoplastic cells from the patient with a PLX-binding agent. Certain embodiments of the methods described herein also include a step of measuring the amount of PLX-binding agent bound to PLX. In some embodiments, the PLX-binding agent comprises an agent selected from the group consisting of lectins, antibodies and other carbohydrate-specific binding compounds. In a preferred embodiment, the PLX-binding agent comprises a lectin from *Lycopersicon esculentum* (LEL).

In some embodiments, the PLX-binding agent comprises a label, wherein the label is selected from the group consisting of a fluorescent label, a chemiluminescent label, a radioactive label, a magnetic label, a paramagnetic label, a promagnetic label, a colorometric label, an electronic label and a digital label. In certain embodiments, the PLX is expressed on a glycoconjugate.

In some embodiments of the methods described herein, the neoplastic cells from the patient are selected from the group consisting of carcinoma, lymphoma, melanoma, sarcoma, leukemia, retinoblastoma, myeloma, glioma, mesothelioma osteosarcoma, transitional cell carcinoma, squamous cell carcinoma (SCC), carcinomatosis and germinal specimens.

Further embodiments of the present invention include methods of predicting the effectiveness of a drug on neoplastic cells from a patient. Some embodiments comprise the steps of determining the amount of AD6 expression and/or PLX expression on the surface of the neoplastic cells from the patient. The data from the AD6 expression levels on the candidate neoplastic cells relative to standard values for drug response with respect to AD6 expression levels determines a degree of drug responsiveness for the candidate neoplastic cells. The data from the PLX expression levels on the same candidate neoplastic cells from the patient relative to standard values for drug response with respect to PLX expression levels indicates another degree of drug responsiveness for the candidate neoplastic cells. If the degree of drug responsiveness determined by AD6 expression levels is consistent with the degree of drug responsiveness determined by PLX expression levels, the cumulative data from both AD6 and PLX expression levels indicates the rate of drug efficacy on the candidate neoplastic cells with a high degree of accuracy.

In some embodiments of the methods described herein, the standard values for each of the AD6 and PLX drug responsiveness may be adapted to charts or diagrams that are independently represent the standard values for each of the AD6 or PLX. The standard values for each of the AD6 and PLX diagrams are defined based on the algorithms that are developed from the AD6 and PLX expression levels analysis of the statistically significant number of a retrospective set of neoplastic cells of the same cell type as the candidate neoplastic cells from patient.

In some embodiments of the methods described herein, determining the amount of AD6 expressed on the surface of the neoplastic cells from the patient comprises contacting the neoplastic cells from the patient with a AD6-binding agent. Certain embodiments of the methods described herein also include a step of measuring the amount of AD6-binding agent bound to AD6. In some embodiments, the AD6-binding agent comprises an agent selected from the group consisting of lectins, antibodies and other carbohydrate-specific binding compounds. In other embodiments, the AD6-binding agent comprises a label. In some such embodiments, the label is selected from the group consisting of a fluorescent label, a chemiluminescent label, a radioactive label, a magnetic label, a paramagnetic label, a promagnetic label, a colorometric label, an electronic label and a digital label.

In some embodiments of the methods described herein, determining the amount of PLX expressed on the surface of the neoplastic cells from the patient comprises contacting the neoplastic cells from the patient with a PLX-binding agent. Certain embodiments of the methods described herein also include a step of measuring the amount of PLX-binding agent bound to PLX. In some embodiments, the PLX-binding agent comprises an agent selected from the group consisting of lectins, antibodies and other carbohydrate-specific binding compounds. In a preferred embodiment, the PLX-binding agent comprises a lectin from *Lycopersicon esculentum* (LEL).

In some embodiments, the PLX-binding agent comprises a label. In some such embodiments, the label is selected from the group consisting of a fluorescent label, a chemiluminescent label, a radioactive label, a magnetic label, a paramagnetic label, a promagnetic label, a colorometric label, an electronic label and a digital label. In certain embodiments, the PLX is expressed on a glycoconjugate.

In some embodiments of the methods described herein, the neoplastic cells from the patient are selected from the group consisting of carcinoma, lymphoma, melanoma, sarcoma, leukemia, retinoblastoma, myeloma, glioma, mesothelioma osteosarcoma, transitional cell carcinoma, squamous cell carcinoma (SCC), carcinomatosis and germinal specimens.

Additional embodiments include systems and methods of determining whether cells from a patient are likely to be multiple drug resistant (MDR) neoplastic or damaged cells. In some embodiments, the method comprises the steps of determining the amount of polyLacNAc (PLX) expressed on the surface of candidate MDR neoplastic cells or candidate damaged cells and comparing the amount of PLX expressed on surface of the candidate MDR neoplastic cells or on the surface of the candidate damaged cells to the amount of PLX expressed on the surface of cells that have been determined to be drug sensitive neoplastic cells of the same cell type as the candidate MDR neoplastic cells or that have been determined to be undamaged cells of the same cell type as the candidate damaged cells, wherein a decreased amount of PLX expressed on the surface of the candidate MDR neoplastic cells or on the surface of the candidate damaged cells as compared to the amount of PLX expressed on the surface of the drug sensitive neoplastic cells or the surface of the undamaged cells indicates that the candidate MDR neoplastic cells are likely to be MDR neoplastic cells or that the candidate damaged cells are likely to be damaged cells.

Other embodiments described herein relate to systems and methods for determining whether neoplastic cells from a cancerous tissue of a patient are likely to develop multiple drug resistance (MDR). In some such embodiments, the methods can comprise determining the amount of PLX expressed on the surface of a first sample of neoplastic cells from a cancerous tissue from a patient; determining the amount of PLX expressed on the surface of a second sample of neoplastic cells from the cancerous tissue after the patient has been treated with a chemotherapeutic agent for the treatment of cancer; and comparing the amount of PLX-expressed on the surface of the first sample of neoplastic cells to the amount of PLX-expressed on the surface of the second sample of neoplastic cells, wherein a decreased amount of PLX expressed on the surface of the second sample of neoplastic cells as compared to the amount of PLX expressed on the surface of the first sample of neoplastic cells indicates that the neoplastic cells of the cancerous tissue are likely to be MDR neoplastic cells.

Further embodiments include methods of determining whether neoplastic cells are likely to be multiple drug resistant (MDR) neoplastic cells. In some embodiments the methods can comprise determining the amount of PLX expression on the surface of candidate MDR neoplastic cells and comparing the amount of PLX-expression on the surface of the candidate MDR neoplastic cells to the amount of PLX expression known to be on the surface of cells that have been determined to be a drug sensitive neoplastic cells of the same cell type as the candidate MDR neoplastic cells, wherein a decreased in PLX expression level on the surface of the candidate MDR neoplastic cells as compared to the amount of PLX expression level known to be on the surface of cells that have been determined to be drug sensitive neoplastic cells of the same cell type as the candidate MDR neoplastic cells indicates that the candidate MDR neoplastic cells are likely to be MDR neoplastic cells.

Still further embodiments relate to methods of predicting the effectiveness of a drug on neoplastic cells from a patient. In some embodiments, the methods comprise the steps of determining the amount of PLX expression on the surface of the neoplastic cells from the patient and comparing the amount of PLX expressed on the surface of the neoplastic cells from the patient to standard values of the amount of PLX expressed on the surface of neoplastic cells that are of the same cell type as the neoplastic cells from the patient and that have a known history of drug response, wherein the amount of PLX expressed on the surface of the neoplastic cells from the patient relative to the standard values of the amount of PLX determines the rate of the drug efficacy of the neoplastic cells from the patient.

Yet further embodiments include methods of predicting the effectiveness of a drug on neoplastic cells from a patient. Some embodiments comprise the steps of determining the amount of AD6 expression and PLX expression on the surface of the neoplastic cells from the patient and comparing the amount of AD6 and the amount of PLX expressed on the surface of the neoplastic cells from the patient to standard values of the amount AD6 and the amount of PLX expressed on the surface of neoplastic cells that are of the same cell type as the neoplastic cells from the patient and that have a known history of drug response, wherein the amount of AD6 and the amount of PLX expressed on the surface of the neoplastic cells from the patient relative to the standard values of the amount of AD6 and the amount of PLX determines the rate of the drug efficacy of the neoplastic cells from the patient.

Additional embodiments of the invention relate to a system for monitoring drug efficacy. Some embodiments relate to a kit having a binding agent for AD6 and/or a binding agent for PLX and information regarding standard values of the amount of AD6 and/or the amount of PLX expressed on the surface of neoplastic cells of various types that have a known history of drug response, or information describing where to obtain standard values of the amount of AD6 and/or the amount of PLX expressed on the surface of neoplastic cells of various types that have a known history of drug response.

In some embodiments, the standard values of the drug response with respect to the PLX expression levels or the AD6 expression levels, which are determined for a statistically significant number of selected retrospective set of neoplastic cells with a known history of drug response, are adapted to charts or diagrams that display the PLX and AD6 related drug response.

In some embodiments, the PLX and AD6 charts or diagrams are accompanied with the binding agents and instructions to detect and determine the AD6 and the PLX expression levels on the cell surface of candidate specimens and evaluate the degree of drug responsiveness of the candidate specimens relative to the PLX and AD6 standard value charts or diagrams.

In some embodiments, the AD6 binding agent comprises a lectin from *Sambucus nigra* (SNA). In some embodiments, the PLX binding agent comprises a lectin from *Lycopersicon esculentum* (LEL). In certain embodiments, the AD6 binding agent and the PLX binding agent are present together in the same container. In other embodiments, the AD6 binding agent and the PLX binding agent are present in separate containers.

BRIEF DESCRIPTION OF THE DRAWINGS

FIG. 3: The clinical-correlation of the polyLacNAc (PLX) over-expression with drug response on retrospective ovarian cancer specimens, assayed by LEL-binding (SepeX test). A) LEL-binding assay on paraffin sections of four drug-sensitive ovarian cancer specimens, black arrows which point to foci of carcinoma with neoplastic cells which stained, with this detection system. The left column shows images of serial sections that received secondary reagent alone, as a negative control for the assay, with no staining; B) LEL-binding assay on paraffin sections of four drug-resistant ovarian cancer specimens, no detectable LEL-staining was seen with neoplastic cells on resistant specimens. The left column shows images of serial sections that received secondary reagent alone, as a negative control for the assay, with no staining.

DETAILED DESCRIPTION

Resistance to cytotoxic agents is a common clinical problem in the treatment of neoplastic or damaged cells. "Multidrug resistant" and "multidrug resistance" (MDR) are referred to resistance of neoplastic cell or damaged cell to a number of different drugs. Such cells have a reduced efficacy for many drugs, including drugs to which the neoplastic cell or damaged cell was never exposed. MDR cells commonly exhibit a decrease in drug accumulation due to reduced uptake and increased efflux in resistant cells. That is because the tumor cells, even within the same type of cancer, show different molecular characteristics that affect their responses to drugs. The molecular differences are the results of the genetic and epigenetic specificities in different individuals. Many patients die because the treatment they receive is not compatible with the molecular specificity of their tumors.

As used herein, the term "patient" can refer to a subject that is being treated, diagnosed or otherwise tested. Subjects can include humans as well as animals included for veterinary uses, such as small animals, farm animals and zoo animals. Patients carrying MDR cells are often treated with drugs without effective results. Drug resistance, thus, has been an unquestionable dilemma in cancer chemotherapy. Despite the importance for molecular specificity in cancer treatments, standard chemotherapy regimens are, yet, lacking prognostic tests that help physicians to select suitable treatment strategy for personalized chemotherapy.

In some embodiments of the methods and systems described herein, when used in connection with a biomarker, specified molecule or class of molecules, the term "amount" can refer to the number of molecules of the biomarker molecule, the number of molecules of the specified molecule or the number of molecules falling within the class of molecules present at a particular location, for example, at the cell surface. In other embodiments, the term amount can refer to the mass or weight of the biomarker, the mass or weight of the specified molecule or the mass or weight of molecules within the class of molecule. In still other embodiments, the term amount can refer to the content of the marker, the content of the specified molecules or the content of molecules within the class or molecules at a particular location.

In some embodiments of the methods and systems described herein, damaged cells can include MDR damaged cells. In other embodiments, damaged cells include only MDR damaged cells.

The methods and systems described herein address the crucial unmet clinical need of predicting drug response before administrating the chemotherapeutic drugs that may be ineffective to the tumor or damaged cells. Our method is based on the identification of a glycan biomarker that it's cell surface expression levels on neoplastic cells or damaged cells is associated with drug response of these neoplastic cells or damaged cells. The data obtained from probing the amounts of glycan biomarker on a statistically significant number of retrospective set of specimens from a defined neoplastic cell types with a known history of drug response, and the correlation of the amounts of the biomarker with the degree of drug responsiveness of the tested cells enables developing algorithms for evaluating drug responsiveness and drug efficacy on neoplastic cells or damaged cells from patients. The algorithms for evaluating drug responsiveness are developed by analyzing the PLX expression levels on a statistically significant number of retrospective set of a selected neoplastic or damaged cell types with a known history of drug response. The developed algorithms for evaluating drug-response of a defined cell type can be used to characterize the standard values for drug response of a defined cell type. The standard values for the defined cell types can be adapted to the standard chart, standard diagram or standard curve, which are used as indicators for drug response by candidate neoplastic or damaged cells from patients, as well as using as index to determine the rate of drug efficacy on neoplastic or damaged cells.

Probing the biomarker distribution on damaged cells provides molecular guidance for selecting suitable treatment strategies for each patient. Up to this date, all efforts to identify proteins or genomic elements as biomarkers for drug response in standard chemotherapy have remained less successful. Described here is a system that is developed for predicting drug response based on a biomarker which is identified as glycan motif on human cell surface. This glycan motif, herein after PLX, is associated with drug response.

Some embodiments of the present invention relate to methods and systems for providing guidance for treatment strategy in neoplastic and damaged cells.

Some embodiments of the present invention relate to predict drug effectiveness in chemotherapy of neoplastic and damaged cells. Other aspects of the invention described herein relate to a new cell surface glycan biomarker for drug response, which is termed PLX, that can be utilized in developing methods and systems in forms of algorithms and standard values to predict drug response and determine the rate of drug efficacy on neoplastic and damaged cells. In some embodiments, the association of the PLX expression level with drug response in malignant tissues can be verified by histochemical methods.

As used herein, the term "PLX" refers to the N-acetyl-lactosamine (-Galβ1-4GlcNAc-)n oligomers that are known as polylactosamine (Poly-lacNAc) glycans. Poly-lacNAcs comprise 2, 3, 4 or higher number of lactosamine disaccharide repeats that appear on various cell membrane glycoconjugates and are involved in various cell-signaling reactions (20-21).

The presence of poly-lacNAcs in different moieties can be detected by various glycan-binding agents including natural and recombinant plant and animal lectins, monoclonal and polyclonal anti-glycan antibodies, as well as synthetic chemical compounds that can interact with PLX. The glycan-binding agents can include, but are not limited to, *Lycopersicon esculentum* LEL, *Griffonia simplicifolia* agglutinin II (GSA-II), Phytohemagglutinin lectins (PHA-L and PHA-E), carbohydrate binding protein 30 (CBP30), *Datura stramonium* lectin (DSL), selectin series of glycan binding proteins, galectin series of glycan binding proteins, antiglycan antibody A5, antiglycan antibody C6, anti I-antigen, and anti-i-antigen series of antibodies, NUH2 antibody, and ACFH18 antibody.

The PLX binding agents can be detected via label-free methodologies, or can be tagged or activated with general labeling systems, including horse radish peroxidase (HRP), alkaline phosphatase (AP), biotinylation, flourescin labeling, radiolabeling, electro and magnetic labeling. PLX-binding activities can be identified in soluble and solid samples by variety of detecting methods including, histochemistry, fluorescent cell sorting (flow cytometry), Enzyme-linked immunosorbent assay (ELISA), Radioimmunoassay (IRA), microarray-based technology, magnetic beads assay, chemical beads assay, polymer- and dendromer-based methodologies.

Data obtained from histochemical staining of a retrospective set of human cancer tissue sections confirmed the association of the PLX over-expression with drug response on these specimens. Therefore, PLX is an indicator whose expression level on the cells is associated with drug response in chemotherapy of neoplastic and damaged cells. Accordingly, some embodiments of the present invention provide procedures and a system to evaluate the responsiveness of neoplastic and damaged cells to chemotherapeutic drugs by utilizing the data obtained from the PLX expression levels on neoplastic and damaged cells and evaluating these data with the developed algorithms and standard values for drug response to predict drug responsiveness by candidate neoplastic and damage cells and the rate of drug efficacies on the candidate neoplastic and damaged cells. This system can reliably assess the efficacy of drugs in chemotherapy by probing the PLX distribution on malignant and damaged cells and utilizing this information in algorithms that has been developed to define standard values demonstrating the correlation of the PLX expression levels with chemotherapeutic drug response by neoplastic and damaged cells with a known history of drug response.

The methods and systems described herein can be used with various cell types, including, but not limited to, carcinoma, lymphoma, melanoma, sarcoma, leukemia, retinoblastoma, myeloma, glioma, mesothelioma, osteosarcoma, transitional cell carcinoma, squamous cell carcinoma (SCC), carcinomatosis and germinal cell tumors.

In some embodiments, the tests distinguish patients that are at risk of developing drug resistance before starting chemotherapy. In other embodiments, this test can also be used for monitoring the drug effectiveness and tumor progression in the course of treatments. Such evaluation can be performed with respect to "standard values." The standard values can be calculated based on algorithms developed from data obtained from the PLX expression levels analysis of a series of statistically significant number of specimens from a defined cell types, including undamaged cells, non neoplastic cells, as well as the neoplastic cells with known history of drug response of the defined cell types.

Example 1

A lectin-histochemistry method with *Lycopersicon esculentum* lectin (LEL) was adapted to probe the PLX expression on human tissue sections. This method is referred to as the "SepeX" test. The data obtained from testing a retrospective set of human ovarian cancer specimens with known history of drug-response demonstrated a striking correlation between the PLX over-expression on these specimens with drug responsiveness of the samples.

The clinical correlation of the PLX over-expression with drug responsiveness was elucidated in the course of clinical validation of AD6. AD6 is the multi-drug resistance glycan biomarker, which was detected by flow cytometry methods, and which was described in U.S. Pat. No. 7,585,503, the disclosure of which is incorporated herein by reference in its entirety. The AD6 clinical correlation with drug response was studied by lectin-histochemical methods on human normal and malignant tissue specimens. The histochemical studies on clinical specimens, consistent with previous results by flow-cytometry, confirmed the clinical correlation of the AD6 overexpression with drug responsiveness (see Results).

The correlation between PLX and drug response was tested by screening the retrospective set of twenty-four human ovarian cancer tumor specimens, with known history of drug response, for the PLX expression level by SepeX method. The data showed a significant clinical correlation between the PLX expression level and the drug response in these samples, where 92% of the drug susceptible samples showed PLX over expression and 75% of the resistant samples were PLX-negative (see table 1.)

Experimental Procedures

Figure 1:
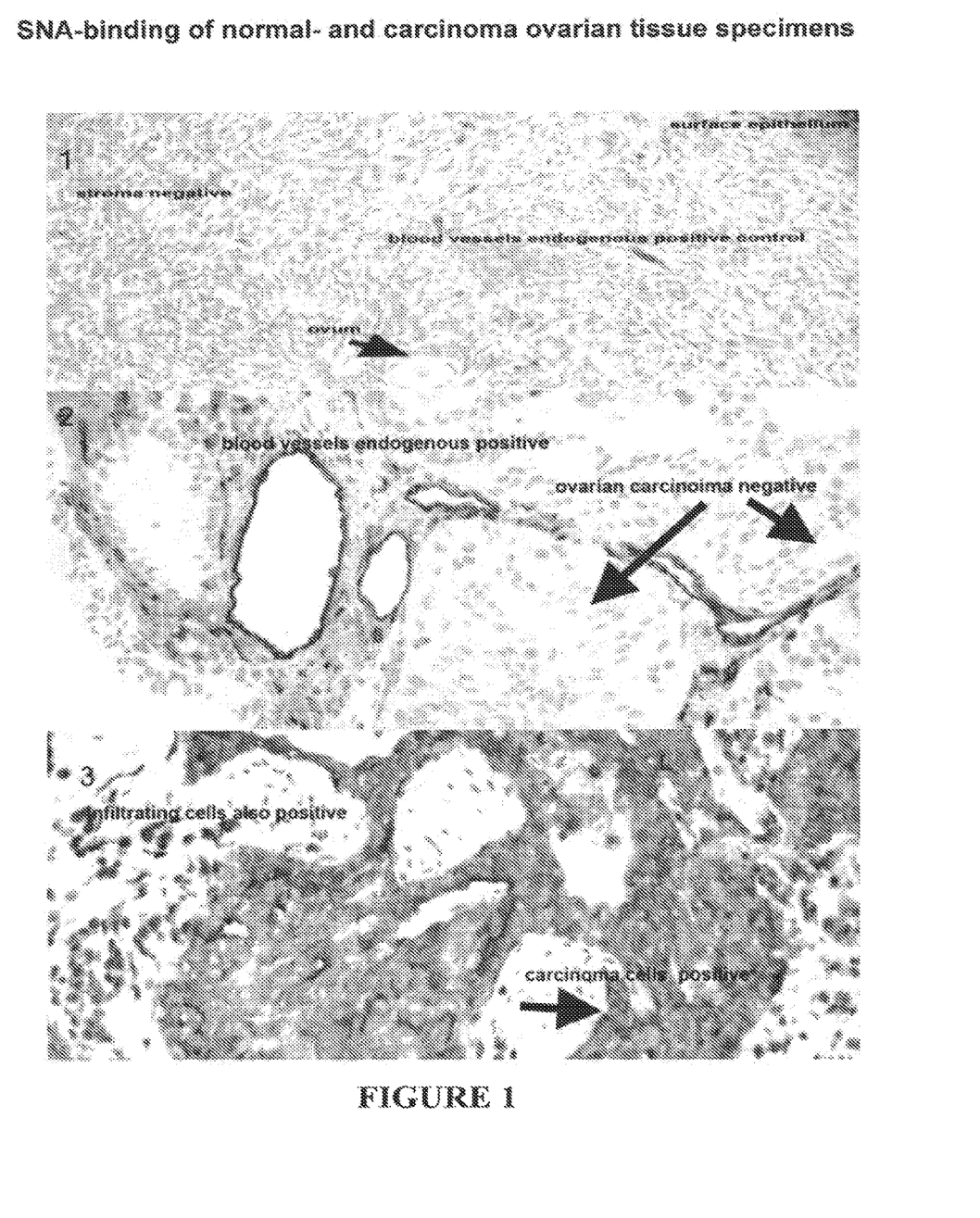
FIG. 1: SNA-binding (SetaX test) of paraffin sections of normal and malignant ovarian tissue specimens. 1) Normal ovarian negative for SNA, 2) Malignant ovarian negative for SNA (drug-resistant candidate), blood vessels staining used as internal SNA-positive control, 3) Malignant ovarian section positive for SNA, including SNA-positive infiltrating cells (drug-sensitive candidate).

Lectin-Histochemistry Procedure
Reagents:
Biotinylated LEL 1:5000 (Vector labs B1175- *Lycopersicon esculentum*)
Biotinylated SNA 1:500 (Vector Labs B1305-elderberry bark lectin)
Alkaline phosphatase labeled—or Horse Radish peroxidase labeled—streptavidin 1:500 (Jackson labs 016-050-084)
Vector Blue in 0.1M Tris/levimasole—Vector labs SK-5300 Alkaline phosphatase substrate III
Nuclear Fast Red (Vector labs)
Assay Procedure Paraffin sections of selected specimens was deparaffinized, blocked, and overlaid with predetermined concentrations of biotinylated *Sambucus nigra* agglutinin (SNA) lectin or biotinylated *Lycopersicon esculentum* (LEL) or with control reagent. Binding was detected by horse-radish peroxidase labeled streptavidin, or alkaline phosphatase labeled streptavidin, using Vector blue substrate, nuclear fast red counterstaining, and aqueous mounting. Samples were washed with Tris-buffered saline containing 0.2% Tween and 1% bovine serum albumin to block nonspecific binding. Digital photomicrographs were taken while viewing with an Olympus BH2 microscope with a MacroFire camera and Adobe Photoshop.
Lectin-Binding Protocol
Materials:
1. Paraffin sections of ovarian samples
2. Wash buffer:
0.05M Tris HCl/150 mM NaCl pH 8.0/0.1% Tween 20
Add $CaCl_2$ (10 mM) and $MnCl_2$ (10 mM) just before assay
3. Diluting buffer: wash buffer with 1% BSA: 500 mg/50 ml of wash buffer
Procedure:
1. Deparaffinize and rehydrate: xylene-3 changes, 100% alcohol—3 changes; 95% alcohol—3 changes, 70% alcohol—3 changes
2. TBS washes×3
3. If using frozen sections:
   a) overlay with 0.1% avidin/PBS for 15 minutes; TBST washes×3
   c) overlay with 0.01% biotin/PBS for 15 minutes; TBST washes×3
4. overlay with negative control or with diluted lectin:
   a) diluting buffer control slide
   b) biotinylated LEL 1:5000 (*Lycopersicon esculentum*-tomato lectin)
   c) biotinylated SNA 1:1000 (elderberry bark lectin)
5. incubate 30 minutes at room temperature; wash in 3 changes of wash buffer
7. overlay with alkaline phosphatase labeled streptavidin 1:500 in diluting buffer OR, with HRP-streptavidin 1:500 in diluting buffer)
8. incubate for 30 minutes at room temperature; wash in 3 changes of washing buffer.
9. Make fresh substrate; overlay with substrate for 3-5 minutes (Vector Blue in 0.1M Tris/levimasole—Vector labs SK-5300 Alkaline phosphatase substrate III)
11. wash with 3 changes of wash buffer
12. counterstain in nuclear fast red for 30 minutes OR Meyer's hematoxylin for 3 minutes;
13. wash with 3 changes of wash buffer
14. coverslip with aquamount
Results
The Clinical-Correlation of the AD6 Over-Expression with Drug Response—Further Confirmation of AD6 as a Biomarker for Drug Response Lectin-histochemistry method with SNA staining was adapted to assess the AD6 expression level on human ovarian epithelial tissues. We selected the name "SetaX" for this SNA-binding method. We screened forty paraffin sections from ovarian normal and malignant clinical specimens to evaluate the AD6 expression level on these samples. Table 1, summarizes the list of various specimens and the results of the SetaX test on these samples. Paraffin slides of ten human ovarian normal sections, twenty-two ovarian malignant specimens (no history of drug response) and eight malignant samples with known history of drug response were tested for AD6 expression level. FIG. 1 displays the SNA-binding pattern of paraffin sections from normal and malignant ovarian specimens with negative- and positive-binding patterns to SNA. A positive SNA-binding, SetaX reflects the AD6 over-expression on tissues to indicate the drug susceptibility.

TABLE 1

The results of screening sixty four paraffin sections of human ovarian specimens for the AD6 and PLX expression-levels. Samples were tested by lectin-histochemical methods for AD6 detection "Setax test" and PLX detection "SepeX test."

| Human Ovarian tissue type | No. of samples | AD6 (+) | AD6 (−) | PLX (+) | PLX (−) |
|---|---|---|---|---|---|
| Normal | 10 | 0 | 10 | 0 | 10 |
| Cancer (no drug-response history) | 22 | 9 | 11 | Not tested | Not tested |

TABLE 1-continued

The results of screening sixty four paraffin sections of human ovarian specimens for the AD6 and PLX expression-levels. Samples were tested by lectin-histochemical methods for AD6 detection "Setax test" and PLX detection "SepeX test."

| Human Ovarian tissue type | No. of samples | AD6 (+) | AD6 (−) | PLX (+) | PLX (−) |
|---|---|---|---|---|---|
| Cancer (drug sensitive) tested for AD6 | 4 | 3 | 1 | — | — |
| Cancer (drug resistant) tested for AD6 | 4 | 1 | 3 | — | — |
| Cancer (drug sensitive) tested for PLX | 12 | — | — | 11 | 1 |
| Cancer (drug resistant) tested for PLX | 12 | — | — | 3 | 9 |

Figure 2:
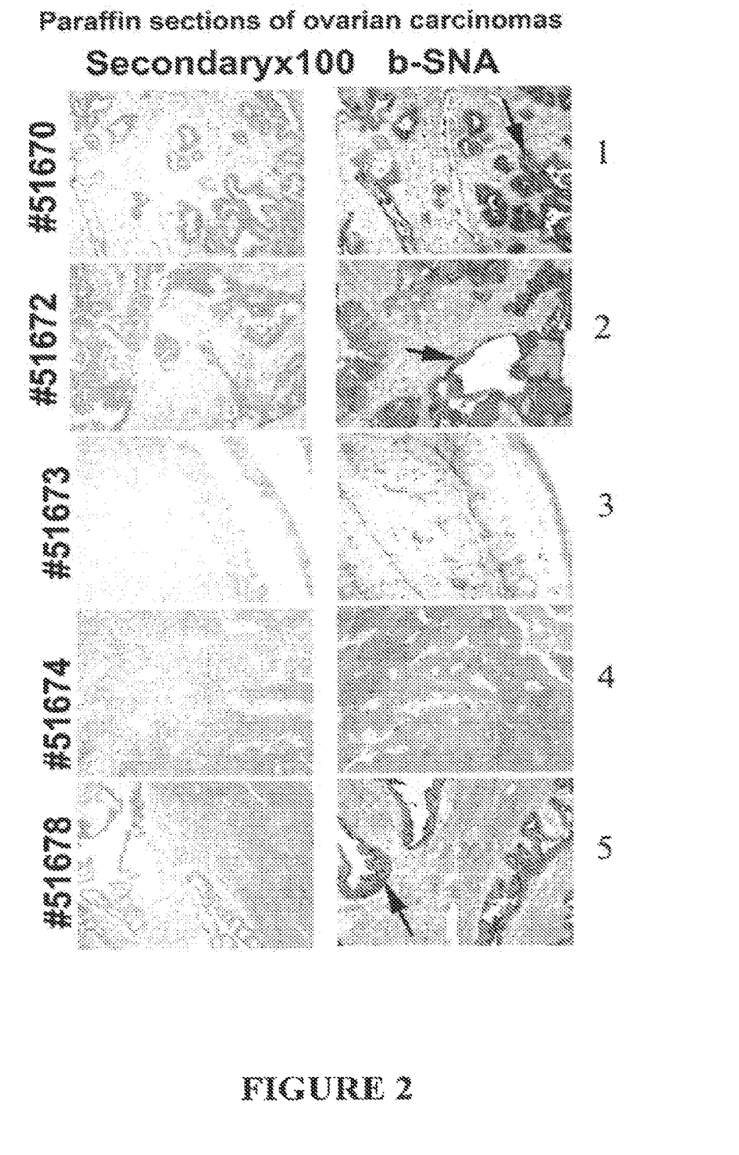
FIG. 2: Demonstration of SNA-binding (SetaX test) to ovarian carcinoma paraffin sections with no history of drug response; The left column shows images of serial sections that received secondary reagent alone, as a negative control for the assay, with no staining. The right column has black arrows, which point to foci of carcinoma with neoplastic cells, which stained, with this detection system. Slides 1, 2 and 5 represent examples of ovarian carcinoma that stained well with the marker, i.e. drug-sensitive candidates. Slides 3 and 4 represent ovarian carcinoma examples of no detectable SNA-staining in carcinoma foci, i.e. drug-resistant candidates.

All of the normal ovarian samples were negative for SNA-staining. From the twenty-two malignant specimens, eleven were negative for SNA binding, nine of them were positive for SNA-binding (i.e. AD6 over-expression) and two samples showed less than 20% SNA binding, which were considered below the, arbitrary, cut-point. FIG. 2, shows several examples of SNA-positive and SNA-negative binding to a set of human malignant ovarian specimens, as prototype of this experiment. The preliminary results showing all negative SNA binding for normal samples, but about 40% negative in malignant samples were highly encouraging and confirmed the clinical applications of this method. Furthermore, the result of 40% SNA-negative for malignant samples was in agreement with clinical consensus for drug response in ovarian cancer patients, per which nearly 40% of patients show resistance to chemotherapy. Interestingly, more support came from the SNA staining of retrospective malignant specimens with known history of drug response. The AD6 expression level of these samples demonstrated significant correlations with drug-susceptibility and drug-resistance. These samples were received as eight coded-slides, four susceptible and four resistant, from the "Tissue repository core" at the University of Pennsylvania. The experiment was performed in investigator-blinded fashion. The AD6 expression level was successfully correlated with drug-susceptibility and drug-resistance for 6 out of 8 coded samples (75% correlation).

Identification of PLX as a New Biomarker for Drug Response—

Figure 3:
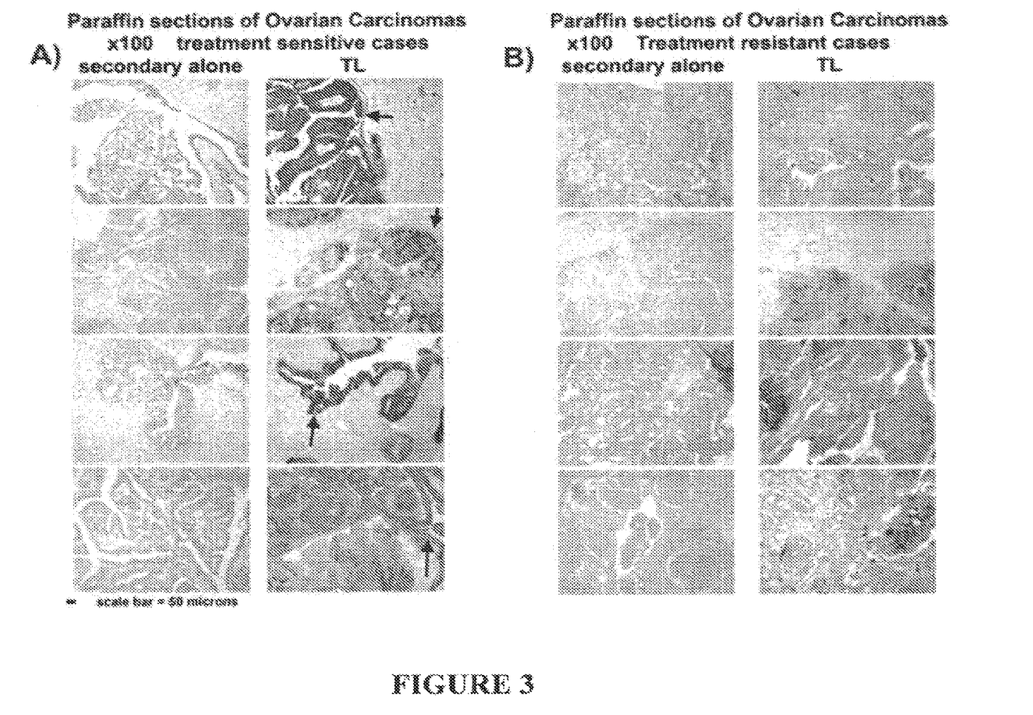

Lectin-histochemistry method with LEL binding assay (SepeX test) was adapted to evaluate the PLX expression levels on a retrospective set of twenty-four human ovarian cancer specimens with known history of drug response (twelve chemo-susceptible and twelve chemo-resistant). LEL is a lectin that specifically binds to N-acetyllactosamin oligomers, with different number of disaccharide units, preferentially to tri-lacNAc and tetra-lacNAc. The experiment was performed in an investigator-blinded fashion with coded slides, similar to what was previously described for SNA-binding assay. The data from Sepex test demonstrated a significant correlation of the amounts of PLX expression level on the tested tumor specimens with actual drug-response known for these samples. According to these results, eleven samples of the twelve chemo-susceptible specimens, showed high PLX expression levels on tumor sections, i.e. PLX over expression (>92%); and nine of the twelve chemo-resistant samples showed very low or no PLX expression on tumor cells, i.e. PLX-negative samples (75%.) FIG. 3, demonstrates histochemical staining of PLX by Sepex method on four drug-sensitive and four drug-resistant ovarian cancer specimens of deparaffinized tissue section slides, to exampilify the PLX over expression and PLX negative samples on human specimens.

The Setax and Sepex tests were adapted as working methods for evaluating the amounts of AD6 and PLX, respectively, on different samples. The working tests, Setax and Sepex, for the AD6 and PLX over-expression assessments, have been optimized and characterized for their variation, reproducibility and sensitivity on clinical samples. The suitability of these tests for clinical utility was confirmed by testing sixty-four human normal and malignant ovarian tissue sections obtained as clinical specimens.

Example 2

The described working tests, Setax and Sepex, that are developed for evaluating the AD6 and PLX expression levels respectively, are used to screen a statistically significant number of specimens from a cohort of ovarian cancer patients in both retrospective and prospective manners with respect to the patient's response to chemotherapeutic drugs after a defined period of follow up. Ovarian cancer is used as example for experimental studies to validate the methods and systems that are proposed in the present invention. The information obtained from such study provides enough data to develop algorithms to determine the clinical correlation of the biomarkers' expression levels on a series of selected cells with drug response by the same series of selected cells.

The invention, thus, introduces an unprecedented system to predict the response to the first-line drug treatments regimen for cancer chemotherapy. Therefore, the method may save millions of lives as well as providing a great deal of savings in costs, by allowing physicians to select effective personalized chemotherapy for those who may not have benefited from platinum treatments.

Experimental Procedures

Testing Retrospective Specimens with Known History of Drug Response:

The AD6 and PLX expression levels are tested on statistically sufficient number of tumor sections, from a cohort of ovarian cancer patients with a known history of drug response, with the defined specificity as described below in "Specimens' specificity". Determining the correlation of the predicted drug efficacy based on the Setax and Sepex assays with the original known chemo-response by patients indicates the clinical value of our system in predicting drug response. The statistical analysis of the data obtained from this series of experiments provides basis for developing algorithms for drug response assessments. The developed algorithms are used to, 1) define the cut-off points for each of the relevant biomarker's expression level, 2) to determine the sensitivity and specificity of the prognostic tests for drug response and, 3) to define standard values for drug responsiveness for the defined neoplastic cell types.

Testing Neoplastic Specimens from Patients in Prospective Studies:

This study is also in parallel with the retrospective samples analysis and the data regarding cut-off points, sensitivity etc. that are developed from the retrospective studies will be considered in the process of the prospective trial analysis. In this part, the AD6 and PLX expression levels will be tested in a prospective manner on tumor sections obtained at the time of the primary surgery from a cohort of ovarian cancer patients with specificity described in the "Specimens specificity". The patients will then undergo standard chemotherapy treatment and their clinical response are determined based on chemo-sensitivity or chemo-resistance as described in oncology definition by Thigpen, et al. Journal of Clinical Oncology, 1994, 12: 1748. At the conclusion of the prospective phase, after a defined period of follow up, the PLX and AD6 expression values determined in the beginning of the prospective study are correlated with actual drug response, chemo-sensitivity or chemo-resistance, by each patient. The statistical analysis of this information is used to develop algorithms for drug response and to define the standard values for drug response for the defined cancer types, in this case ovarian cancer.

The degree of drug responsiveness or the rate of drug efficacy on a candidate patient from a defined cancer type is predicted by determining the PLX and/or AD6 expression levels of a cancer specimen from a candidate patient before starting chemotherapeutic treatment and evaluating its drug responsiveness relative to the standard values developed from the above mentioned retrospective and prospective studies of statistically significant number of samples of the same cancer type as the cancer type of candidate patient.

Specimen Specificity

Tumor samples are from high grade (grades 2 or 3) primary epithelial ovarian carcinoma of serous, clear cell, and endometrioid subtypes. The specimens are collected at the time of initial cytoreductive surgery. Anatomically, the tumor specimen may originate from the primary ovarian tumor, or from a metastatic focus such as omentum, abdominal/pelvic peritoneal dissemination, or lymph node metastasis. The specimens are selected from patients prior to treatment by first-line chemotherapy with platinum-based drugs, with a known history of their drug response after treatment, with a follow up of five years (see Criteria for drug-sensitivity and drug resistance.)

Criteria for Pt-Drug Sensitivity and Resistance:

The definition of platinum sensitivity and resistance is based on Gynecologic Oncology Group definition (Thigpen, et al. Journal of Clinical Oncology, 1994, 12: 1748). Platinum sensitive disease is defined as at least 6 months of disease free interval from the first-line platinum-based treatment. If the patient recurs in the first 6 months following successful completion of first-line platinum-based regimen, the disease is deemed platinum-resistant. Platinum refractory disease has been defined as progression or persistent of disease while the patient is receiving first-line platinum-based therapy. Patients with resistant, persistent, and refractory disease are usually considered as one group, even though there is still considerable heterogeneity with regard to overall drug sensitivity within these populations.

Statistical Analysis

The objective will be achieved by dividing samples into two groups of drug-sensitive and drug-resistant based on their known history of drug response (see Criteria for Pt-drug sensitivity and resistance). Receiver operating characteristic (ROC) analysis method will be used to calculate the best cut-point for the AD6 and PLX separately, based on the data from the semi quantitative scoring analysis. Overall, ROC analysis produces a graphical plot of the sensitivity and specificity for drug response classification system as its discrimination threshold is varied. It also produced the fraction of true positive rate versus the fraction of false positive rate. ROC analysis provides tools to select possibly optimal models and to discard suboptimal ones independently from (and prior to specifying) the group distribution. We define Sensitivity here as the proportion of actual drug-sensitive which are correctly identified as such (e.g. the percentage of drug-sensitive patients who are identified as having the condition) and Specificity as the proportion of negatives which are correctly identified. A theoretical, optimal prediction can achieve 100% sensitivity and 100% specificity. These analyses will be performed using the SPSS version 19. We will use Chi-square for the binary evaluation of the slides.

Example 3

Data obtained from screening a large number of biopsy specimens with known history of drug response is statistically analyzed to define "standard values" for PLX and AD6 expression levels on retrospective specimens. The algorithm and the standard values are used to determine the prognostic rate for drug efficacy of the patient samples that are not double negative or double positive for PLX and AD6.

This technique offers an unprecedented companion diagnostic procedure that provides molecular guidance for predicting drug responsiveness and drug efficacy on each patient. Embodiments of the present invention introduce a method of personal treatment to a wide spectrum of patients that are treated by standard chemotherapy. The test is useful to detect intrinsic resistance in patients before administrating the drug, as well as those patients that are at high risk to develop resistance. The method can also be used as a prognostic test to monitor the drug resistance that may developing during the course of treatments. Accordingly, the methods and systems described herein can save many lives as well as provide a great deal of savings in costs by allowing physicians to select effective personal chemotherapy for those who may not get benefit from the regular treatments.

All of the documents cited in this specification are incorporated herein by reference in their entireties.

REFERENCES

1—Taylor M E. Drickamer K. Paradigms for glycan-binding receptors in cell adhesion. *Curr Opin Cell Biol.* 2007 19:572-7.

2—Go S. Yoshikawa M. Inokuchi J. Glycoconjugates in the mammalian auditory system. *J Neurochem.* 2011 116756-63

3—Hua S. An H J. Ozcan S. Ro G S. Soares S. DeVere-White R. Lebrilla C B. Comprehensive native glycan profiling with isomer separation and quantitation for the discovery of cancer biomarkers. *Analyst.* 2011, 136:3663-71

4—Zhou. Levery S B. Hsu F F. Wang P G. Teneberg S. Almeida I C. Li Y. Xu H. Wang L X. Xia C. Ibrahim N K. Michael K. Immunologic mapping of glycomes: implications for cancer diagnosis and therapy. *Front Biosci* (Schol Ed). 2011, 3:1520-32

5—Hakomori, S. Tumor-associated carbohydrate antigens defining tumor malignancy: basis for development of anti-cancer vaccines. *Adv. Exp. Med. Biol.* 2001, 491:369-402

6—Kannagi R. Yin J. Miyazaki K. Izawa M. Current relevance of incomplete synthesis and neo-synthesis for cancer-associated alteration of carbohydrate determinants—Hakomori's concepts revisited. *Biochim Biophys Acta.* 2008, 1780:525-31

7—Dube D. H., Bertozzi C. R. Glycans in cancer and inflammation—potential for therapeutics and diagnostics. *Nat. Rev. Drug. Discov.* (2005) 4, 477-88

8—Werz D. B. Seeberger P. H. Carbohydrates as the next frontier in pharmaceutical research. *Chemistry* 2005, 11:3194-206

9—Leeming D J. Bay A C. Vassiliadis E. Larsen M R. Henriksen K. Karsdal M A. Post-translational modifications of the extracellular matrix are key events in cancer progression: opportunities for biochemical marker development. *Biomarkers.* 2011 16:193-205

10—Alavi A. and Axford J. S. The pivotal nature of sugars in normal physiology and disease. *Wien Med Wochenschr* 2006, 156: 19-33

11—Williams S A, Stanley P. Roles for N- and O-glycans in early mouse development. *Adv Exp Med Biol.* 2011, 705:397-410.

12—Alen M M. Kaptein S J. De Burghgraeve T. Balzarini J. Neyts J. Schols D. Antiviral activity of carbohydrate-binding agents and the role of DC-SIGN in dengue virus infection. *Virology.* 2009, 387: 67-75.

13—Molnar J., Demirel Kars M., Gunduz U., Engi H., Schumacher U., Van Damme E. J., Peumans W. J., Makovitzky J., Gyemant N., Molnar P. Interaction of tomato lectin with ABC transporter in cancer cells: Glycosylation confers functional conformation of P-gp. Acta histochemica 2009, 111:329-333

14—Tate M D. Job E R. Brooks AG. Reading PC. Glycosylation of the hemagglutinin modulates the sensitivity of H3N2 influenza viruses to innate proteins in airway secretions and virulence in mice. *Virology.* 2011, 413:84-92

15—Balzarini, J. Targeting the glycans of gp120: a novel approach aimed at the Achilles heel of HIV *Lancet Infect Dis,* 5: 726-731, 2005.

16—Zdenka Sulova Z., Mislovic D. Gibalova L. Vajc Z. Eva Polakova E. Uhri B. Tylkova L. Kovarova Sedla, A. Breier A. Vincristine-induced overexpression of P-glycoprotein in L1210 Cells is associated with remodeling of cell surface saccharides. *J. Proteome Res.* 2009, 8: 513-520

17—Hakomori S I. Glycosynaptic microdomains controlling tumor cell phenotype through alteration of cell growth, adhesion, and motility. *FEBS Lett.* 2010, 584:1901-6.

18—Regina Todeschini A, Hakomori S I. Functional role of glycosphingolipids and gangliosides in control of cell adhesion, motility, and growth, through glycosynaptic microdomains. *Biochim Biophys Acta.* 2008, 1780:421-33

19—U.S. Pat. No. 7,585,503, entitled METHODS AND SYSTEMS FOR PREDICTING DRUG-RESPONSE, issued Sep. 8, 2009.

20—Arthur C. Stowell S. Cummings R. Galectin 8 signaling in leukocytes occurs through interaction with complex-Type N-glycans. *Glycobiology,* 2009, 19:1354-

21—Chandrasekaran A. Srinivasan A. Raman R. Viswanathan K. Raguram S. Tumpey T. M. Sasisekharan V. Sasisekharan, R. Glycan topology determines human adaptation of avian H5N1 virus hemagglutinin. *Nat. Biotechnol.* 2008, 26: 107-13.

What is claimed is:

1. A method for treating ovarian cancer in a patient, the method comprising:
    determining whether the patient has a platinum-based drug susceptible ovarian cancer by:
    obtaining or having obtained a specimen of ovarian cancer from the patient;
    determining or having determined an expression level of poly-N-acetyllactosamine (PLX) in said patient ovarian cancer specimen, wherein said expression level of PLX has been quantitatively assayed, to determine if the ovarian cancer from which the patient specimen was taken is susceptible to a first-line platinum-based drug selected from the group comprising cisplatin and carboplatin, wherein the ovarian cancer from which the patient specimen;
    administering an effective amount of said platinum-based drug to said patient determined to have drug-susceptible ovarian cancer if the ovarian cancer from which the patient specimen was taken is susceptible to a platinum-based drug.

2. The method of claim 1, wherein the expression level of PLX has been quantitatively assayed by a method comprising using a PLX-binding agent selected from the group consisting of *Lycopersicon esculentum* LEL, *Griffonia simplicifolia* agglutinin II (GSA-II), Phytohemagglutinin lectins (PHA-L and PHA-E), carbohydrate binding protein 30 (CBP30), *Datura stramonium* lectin (DSL), selectin series of glycan binding proteins, galectin series of glycan binding proteins, antiglycan antibody A5, antiglycan antibody C6, anti I-antigen, and anti-i-antigen series of antibodies, NUH2 antibody, and ACFH 18 antibody.

3. The method of claim 1, wherein said minimum threshold expression level of PLX was determined by quantitatively assaying an expression level of PLX in a plurality of ovarian cancer specimens susceptible to said platinum-based drug, wherein said plurality of drug-susceptible ovarian cancer specimens are of the same cell type as said patient ovarian cancer specimen but are not from said patient.

4. The method of claim 3, wherein the expression level of PLX has been quantitatively assayed by a method comprising using a PLX-binding agent selected from the group consisting of *Lycopersicon esculentum* LEL, *Griffonia simplicifolia* agglutinin II (GSA-II), Phytohemagglutinin lectins (PHA-L and PHA-E), carbohydrate binding protein 30 (CBP30), *Datura stramonium* lectin (DSL), selectin series of glycan binding proteins, galectin series of glycan binding proteins, antiglycan antibody A5, antiglycan antibody C6, anti I-antigen, and anti-i-antigen series of antibodies, NUH2 antibody, and ACFH 18 antibody.

5. The method of claim 1, wherein the expression level of PLX has been quantitatively assayed by a method comprising:
    obtaining a first plurality of ovarian cancer specimens with a known susceptibility to the platinum-based drug, wherein said first plurality of specimens are sensitive to said platinum-based drug;
    obtaining a second plurality ovarian cancer specimens with a known susceptibility to said platinum-based drug, wherein said second plurality of specimens are resistant to said platinum-based drug, and wherein the first and second plurality of ovarian cancer specimens are of the same cell type;
    quantitatively assaying an expression level of PLX of said first and second plurality of ovarian cancer specimens to determine an average expression level of PLX for said first and second plurality of ovarian cancer specimens.

6. The method of claim 5, wherein the method does not comprise quantitatively assaying an expression level of AD6 of said first and second plurality of ovarian cancer specimens.

7. The method of claim 5, wherein the method further comprises quantitatively assaying an expression level of AD6 in said first and second plurality of ovarian cancer specimens to determine an average expression level of AD6 for said first and second plurality of ovarian cancer specimens.

8. The method of claim 5, further comprising quantitatively assaying an expression level of PLX of a plurality of non-neoplastic specimens of the same cell type as said first and second plurality of ovarian cancer specimens to determine an average expression level of PLX for said plurality of non-neoplastic specimens.

* * * * *